(12) United States Patent
Messenger

(10) Patent No.: US 12,037,308 B2
(45) Date of Patent: Jul. 16, 2024

(54) REMOVAL OF SULFATE FROM MEG STREAMS USING CALCIUM CHLORIDE

(71) Applicant: Cameron International Corporation, Houston, TX (US)

(72) Inventor: Brian Edward Messenger, Hampshire (GB)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 0 days.

(21) Appl. No.: 18/261,362

(22) PCT Filed: Jan. 18, 2022

(86) PCT No.: PCT/US2022/012724
§ 371 (c)(1),
(2) Date: Jul. 13, 2023

(87) PCT Pub. No.: WO2022/155584
PCT Pub. Date: Jul. 21, 2022

(65) Prior Publication Data
US 2023/0406795 A1    Dec. 21, 2023

Related U.S. Application Data

(60) Provisional application No. 63/138,670, filed on Jan. 18, 2021.

(51) Int. Cl.
*C07C 29/76* (2006.01)
*C07C 29/88* (2006.01)

(52) U.S. Cl.
CPC .............. *C07C 29/76* (2013.01); *C07C 29/88* (2013.01)

(58) Field of Classification Search
CPC .......... C07C 29/76; C07C 29/88; C07C 29/80
See application file for complete search history.

(56) References Cited

U.S. PATENT DOCUMENTS 7,232,505 B2    6/2007    Laborie et al.
8,652,304 B2    2/2014    Nazzer
(Continued)

FOREIGN PATENT DOCUMENTS

KR    101795003 B1    11/2017
WO    2009017971 A1    2/2009
(Continued)

OTHER PUBLICATIONS

International Search Report and Written Opinion issued in the PCT Application PCT/US2022/012724, dated May 9, 2022 (9 pages).
(Continued)

*Primary Examiner* — Yate' K Cutliff
(74) *Attorney, Agent, or Firm* — Matthew Goode

(57) ABSTRACT

A MEG recovery process is described, in which a MEG stream is processed by performing a divalent treatment to reduce dissolved divalent cations in the portion of the stream; performing a sulfate treatment to reduce dissolved sulfate ions in the stream, the sulfate treatment comprising adding an underdose of one or more calcium halides, one or more lower calcium carboxylates, or a mixture thereof to a treatment stream; and precipitating calcium sulfate from the treatment stream; performing a solids removal treatment to reduce solids in the stream; and returning the treated stream, depleted in divalent cations, sulfate ions, and solids, to the MEG recovery process.

20 Claims, 8 Drawing Sheets

(56) References Cited

U.S. PATENT DOCUMENTS

| | | | |
|---|---|---|---|
| 8,999,172 | B1 | 4/2015 | Zuback |
| 9,085,477 | B2 | 7/2015 | Banerjee et al. |
| 10,683,219 | B2 | 6/2020 | Messenger |
| 2010/0191023 | A1 | 7/2010 | Chen |
| 2010/0319923 | A1 | 12/2010 | Slabaugh et al. |
| 2011/0094871 | A1 | 4/2011 | Nazzer |
| 2013/0118989 | A1 | 5/2013 | Caires Fernandez |
| 2014/0058140 | A1 | 2/2014 | Phelps et al. |
| 2014/0066668 | A1 | 3/2014 | Lorenz et al. |
| 2014/0235900 | A1 | 8/2014 | Kaasa |
| 2015/0083669 | A1 | 3/2015 | Matherly et al. |
| 2015/0104356 | A1 | 4/2015 | Messenger |
| 2015/0112102 | A1 | 4/2015 | Jensen |
| 2015/0284272 | A1* | 10/2015 | Messenger ............ C02F 1/5245 210/726 |
| 2018/0305282 | A1 | 10/2018 | Messenger |

FOREIGN PATENT DOCUMENTS

| | | | | |
|---|---|---|---|---|
| WO | 2012171554 | A1 | 12/2012 | |
| WO | WO 2015/157118 | * | 10/2013 | ............... C10L 3/10 |
| WO | 2013168077 | A1 | 11/2013 | |
| WO | 2013179236 | A1 | 12/2013 | |
| WO | 2014035937 | A2 | 3/2014 | |
| WO | 2015157118 | A1 | 10/2015 | |

OTHER PUBLICATIONS

Sandengen, K. et al., Prediction of scale potential in ethylene glycol containing solutions, 2006, Conference: 17. International Oil Field Chemistry Symposium, pp. 1-16.

International Search Report and Written Opinion of International Patent Application No. PCT/US2015/024316, dated Jul. 6, 2015 (11 pages).

* cited by examiner

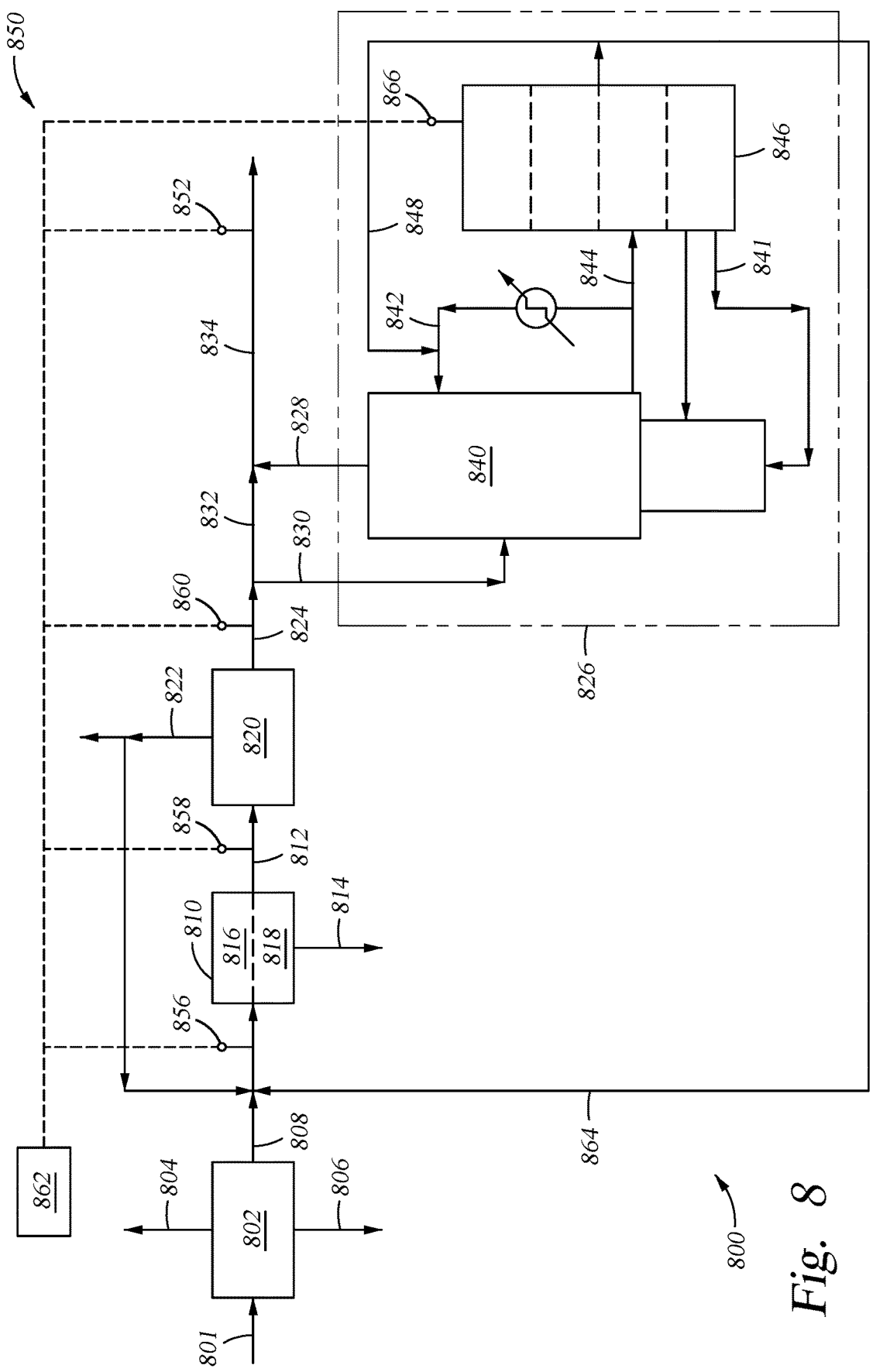

REMOVAL OF SULFATE FROM MEG STREAMS USING CALCIUM CHLORIDE

CROSS-REFERENCE TO RELATED APPLICATIONS

The present application claims priority benefit of U.S. Provisional Application No. 63/138,670, filed on Jan. 18, 2021, the entirety of which is incorporated by reference herein and should be considered part of this specification.

FIELD

This patent application describes methods and apparatus for sulfate ion removal from monoethylene glycol ("MEG") recovery processes. Specifically, use of calcium chloride to remove sulfate ions from MEG stream is described herein.

BACKGROUND

Monoethylene glycol ("MEG") is used in oil and gas processing to suppress formation of hydrate crystals that can complicate hydrocarbon processing operations. MEG is added to produced streams to stabilize the stream for transportation and storage, and then the MEG is removed and recycled. MEG removed from produced streams is processed to remove water, hydrocarbons, and salts before re-use. Salt removal is typically done in two separate processes, one for salts of monovalent cations and another for salts of divalent cations. Monovalent salts are typically removed in a flash reclamation step, in which MEG and water are flashed, leaving a concentrated stream in which monovalent salts precipitate. The precipitated salts are typically removed using various solids removal processes, such as filtration, centrifugation, and cyclonic separation, resulting in a reject stream heavy in salts that is removed from the process.

Divalent salts are typically removed using chemical treatment to precipitate calcium, magnesium, iron, barium, strontium, and other divalent cations. Alkalinity is added to a MEG stream, in the form of hydroxide, bicarbonate, and/or carbonate to precipitate divalent cations as insoluble carbonates and hydroxides. Solids are removed, as above, using solids removal processes to form another reject stream heavy in divalent salts.

The reject streams from monovalent and divalent salt removal stages typically contain enough sulfates to control overall sulfate concentration in the MEG recovery process. When sulfate concentration is high enough, however, sulfates can build up in the process and can cause operating difficulties by increasing density and viscosity of process streams. Barium chloride is known as a chemical treatment to remove sulfates from a MEG stream. The barium chloride precipitates excess sulfates as barium sulfate, which is insoluble in the MEG stream. The barium sulfate is then removed in any of the various solids removal processes described above.

Barium has certain disadvantages as a reagent in MEG processes. The lower solubility of barium chloride requires much water to convey the barium, as barium chloride, to the process, which creates processing burden to carry and then remove the water. The processing burden results in equipment sizing and energy footprint that is large to handle and remove the water. Barium is also expensive and relatively scarce. There is a need for improved sulfate removal for MEG recovery processes.

SUMMARY

Embodiments described herein provide a method of MEG recovery that includes withdrawing a portion of a recycle stream of a MEG vaporization unit; performing a divalent treatment to reduce dissolved divalent cations in the portion of the recycle stream; performing a sulfate treatment to reduce dissolved sulfate ions in the portion of the recycle stream, the sulfate treatment comprising adding an underdose of one or more calcium halides, one or more calcium carboxylates, or a mixture thereof, to a treatment stream; and precipitating calcium sulfate from the treatment stream; performing a solids removal treatment to reduce solids in the portion of the recycle stream; and returning the portion of the recycle stream, depleted in divalent cations, sulfate ions, and solids, to the MEG vaporization unit.

Other embodiments described herein provide a method of MEG recovery that includes withdrawing a portion of a recycle stream of a MEG vaporization unit; performing a divalent treatment to reduce dissolved divalent cations in the portion of the recycle stream; performing a sulfate treatment to reduce dissolved sulfate ions in the portion of the recycle stream, the sulfate treatment comprising adding an underdose of one or more calcium halides to a treatment stream; and precipitating calcium sulfate from the treatment stream; performing a solids removal treatment to reduce solids in the portion of the recycle stream; determining a concentration of calcium ions and a concentration of sulfate ions in the MEG vaporization unit; controlling the sulfate treatment based on the concentration of sulfate ions; controlling the divalent treatment based on pH; and returning the portion of the recycle stream, depleted in divalent cations, sulfate ions, and solids, to the MEG vaporization unit.

Other embodiments described herein provide a method of MEG recovery, comprising withdrawing a portion of a recycle stream of a MEG vaporization unit; performing a divalent treatment to reduce dissolved divalent cations in the portion of the recycle stream; performing a sulfate treatment to reduce dissolved sulfate ions in the portion of the recycle stream, the sulfate treatment comprising adding an underdose of calcium chloride to a treatment stream in a first removal; adding barium chloride to the treatment stream in a second removal; and precipitating calcium sulfate and barium sulfate from the treatment stream; performing a solids removal treatment to reduce solids in the portion of the recycle stream; measuring a first parameter that represents calcium concentration in the MEG vaporization unit; measuring a second parameter that represents sulfate concentration in the MEG vaporization unit; controlling the sulfate treatment based on the second parameter; controlling the divalent treatment based on the first parameter; and returning the portion of the recycle stream, depleted in divalent cations, sulfate ions, and solids, to the MEG vaporization unit.

BRIEF DESCRIPTION OF THE DRAWINGS

FIG. 8 is a schematic process diagram summarizing a MEG recovery process according to another embodiment.

DETAILED DESCRIPTION

Figure 1:
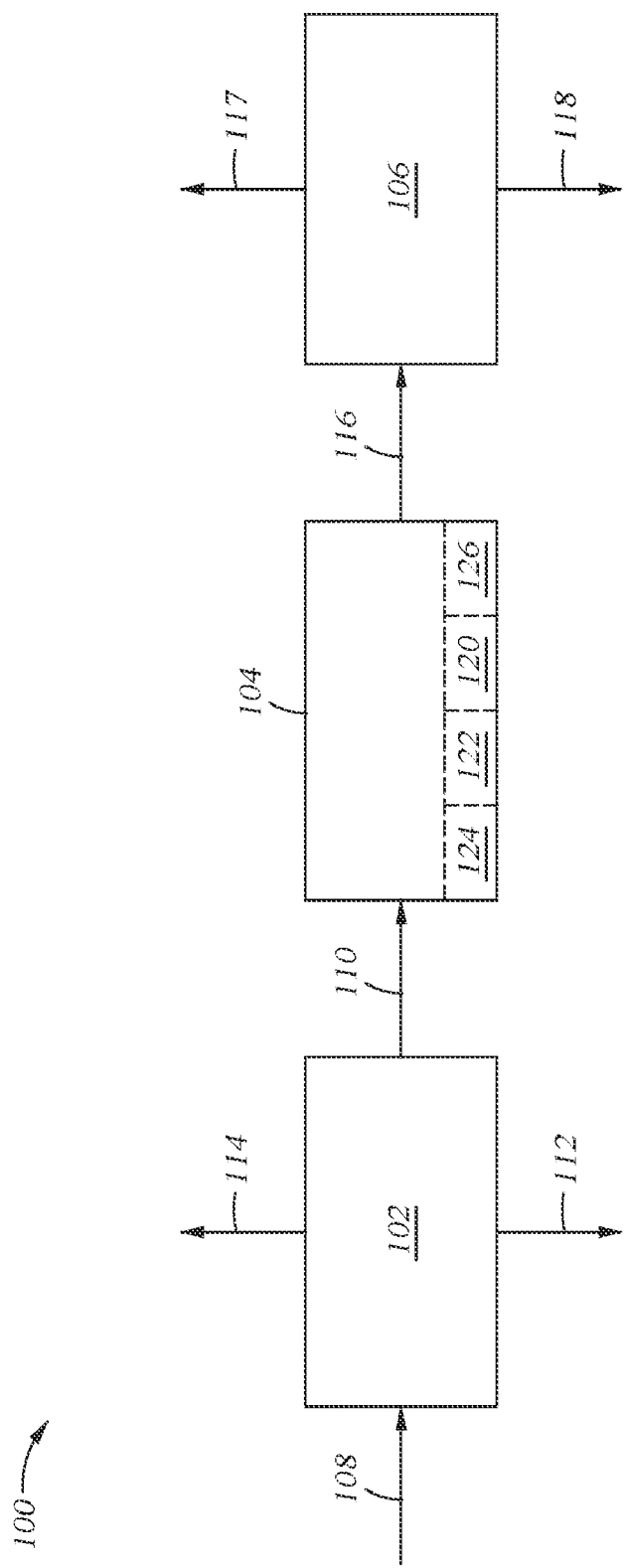
FIG. 1 is a process diagram summarizing a MEG recovery process according to one embodiment.

FIG. 1 is a process diagram summarizing a MEG recovery process 100 according to one embodiment. The MEG recovery process 100 includes a hydrocarbon separation 102, a vaporization 104, and a distillation 106. The hydrocarbon separation 102 receives a rich MEG stream 108 and, in this case, separates three phases. A first liquid phase separates into a first effluent 110, a second liquid phase separates into a second effluent 112, and a gas phase separates into a third effluent 114. The second liquid phase and the gas phase are typically hydrocarbon or hydrocarbon-rich. The first liquid phase predominates in MEG and water, with dissolved and precipitated salts.

The first effluent 110 is routed to the vaporization 104 where MEG and water are vaporized to concentrate monovalent salts in an unvaporized liquid phase. Vaporized MEG and water are routed through a crude MEG line 116 to the distillation 106, where a water stream 117 is removed overhead and a lean MEG stream 118 is withdrawn bottoms and routed to storage or reuse.

Salt, and other impurity, removal is associated with the vaporization 104. A solids removal unit 120 receives a stream from the vaporization 104 and removes solids, such as precipitated salts, from the stream, which is returned to the vaporization 104. As noted above, the vaporization 104 precipitates monovalent salts by concentrating salts in the unvaporized liquid. A divalent treatment unit 122 uses alkalinity, as described above, to precipitate divalent cations as solid salts, thus reducing dissolved divalent cations. The divalent treatment unit 122 may include a solids removal unit to remove the precipitated salt. Thus, the divalent treatment unit 122 can be a divalent removal unit that performs a divalent removal treatment resulting in a stream depleted of divalent cations. A sulfate treatment unit 124 uses a chemical treatment with calcium chloride to precipitate excess sulfates as solid salts, thus reducing dissolved sulfate ions. The resulting calcium sulfate precipitate is removed using a solids removal unit, which may be the solids removal unit of the divalent treatment unit 122 or another solids removal unit or stage. A carboxylate removal unit 126 may also be associated with the vaporization. The carboxylate removal unit 126 acidifies a stream from the vaporization to convert carboxylates into carboxylic acids, which are vaporized and removed from the stream. All the units 120, 122, 124, and 126 that may be associated with the vaporization 104 receive a stream of the unvaporized liquid from the vaporization 104, perform their various treatments, and return the stream to the vaporization individually, collectively, or in groups. It should be noted that the operations performed by the associated units may be performed in any order, and in series or parallel, with the proviso that precipitated divalent salts will be re-dissolved if not removed before acidifying. Thus, one of the associated units may receive a stream from another of the associated units, rather than directly from the vaporization. In one embodiment, for example, the divalent treatment unit 122 receives a stream from the vaporization 104 and routes an effluent to the sulfate treatment unit 124. The sulfate removal unit 124 then routes a stream to the solid removal unit 120. The solids removal unit 120 then routes a stream to the carboxylate removal unit 126. Thus, in this example, divalent treatment, sulfate treatment, and solids removal are performed sequentially, with carboxylate removal thereafter. In general, divalent treatment, sulfate treatment, and solids removal can be performed sequentially in all embodiments herein.

It should be noted that the solids removal unit 120 is shown as a single unit, but could be multiple units. For example, two or more solids removal units can be provided and used in any configuration or arrangement with the other units 122, 124, and 126. One scenario that might use multiple solids removal units is a scenario in which particle sizes produced by the various units are very different. In such a scenario different solids removal units might be used to remove different particle sizes or particle size distributions. Alternately, a single solids removal unit might have multiple solids removal stages that can remove different particle sizes or particle size distributions. Thus, if the vaporization 104 produces particles having different sizes than the particles produced by the divalent treatment unit 122 and/or the sulfate treatment unit 124, multiple solids removal units or stages can be used to remove the particles.

Figure 2:
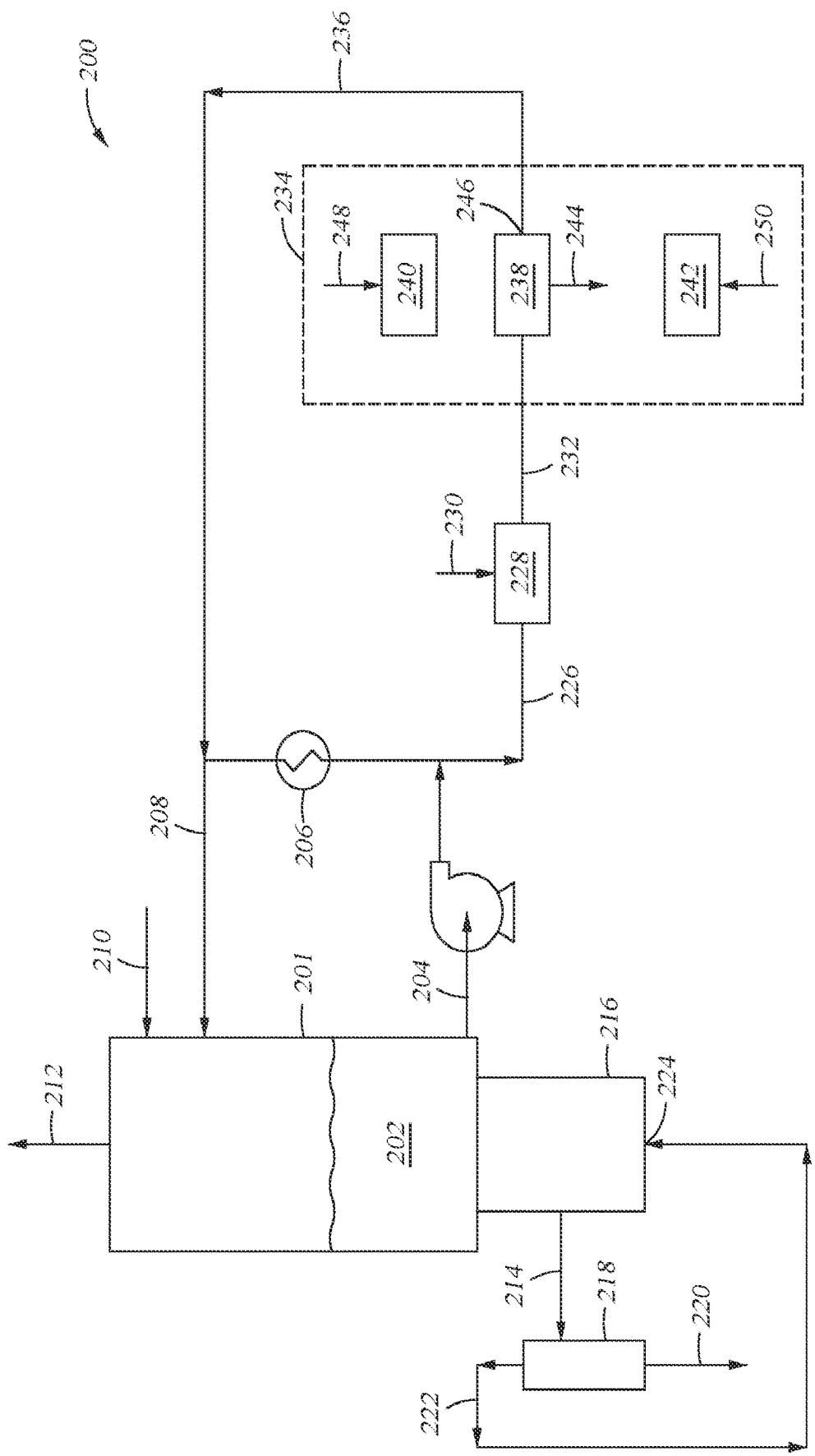
FIG. 2 is a schematic process diagram summarizing a MEG vaporization process with sulfate removal according to one embodiment.

FIG. 2 is a schematic process diagram summarizing a MEG vaporization process 200 with sulfate removal according to one embodiment. The MEG vaporization process 200 may be used as the vaporization 104 in the process 100 of FIG. 1. A vaporization vessel 201 vaporizes a MEG/water mixture from a liquid pool 202 maintained in the vessel 201. A stream of the liquid pool 202 is withdrawn in a recycle 204, which is pumped through a heater 206 and returned to the vessel 201 in a return line 208, which is a heated recycle line. A MEG feed line 210 adds feed to the vessel 201. A vaporized MEG/water mixture exits the vessel 201 through an overhead line 212, which may route the vaporized MEG/water mixture to distillation, as in FIG. 1. In some configurations, water may be removed from a MEG/water mixture prior to vaporization so that a reduced water MEG stream is provided to the vessel 201. In such cases, the MEG/water stream exits through the overhead line 212 and is condensed, and distillation can be avoided, prior to being collected, stored, and reused.

The liquid pool 202 contains precipitated salt, as described above. A salt treatment stream 214 of the liquid pool 202 is withdrawn from a lower portion 216 of the vessel 201 and routed to a solids removal unit 218, which may be one or more of a cyclone, centrifuge, filter, membrane unit, or a combination thereof. Water may be added to the solids removal unit 218 to aid separation. Separated solids, including salts, are removed from the solids removal unit 218 in a separated solids stream 220, while separated liquid is removed in a separated liquids stream 222, which is returned to the vessel 201. In this case the separated liquid stream 222 is returned to the vessel 201 at a bottom location 224 thereof.

A treatment stream 226 may be withdrawn from the recycle 204 to remove unwanted species which accumulate during the vaporization process. The treatment stream 226 is routed to a divalent treatment unit 228. A divalent precipitation reagent stream 230 is added to the divalent treatment unit 228. The divalent precipitation reagent stream 230 contains caustic components such as carbonates, bicarbonates, and hydroxides (e.g. sodium, potassium) that precipitate divalent cations as hydroxide and/or carbonate salts, thus reducing the concentration of dissolved divalent cations. A precipitate stream 232 leaves the divalent treatment unit 228 and is routed to a cleanup section 234, where precipitated solids are removed, along with other impurities. A clean recycle stream 236 is returned to the recycle 204 for routing to the vessel 201.

The cleanup section 234 includes at least a solids removal unit 238 and a sulfate treatment unit 240. One or more additional cleanup units 242, which may include a carboxylate removal unit may be included in the cleanup section 234. The solids removal unit 238 may include any or all of a centrifuge, a cyclone, a filter unit, and a membrane unit. A solids removal stream 244 leaves the solids removal unit 238. A reduced-solids stream 246 also leaves the solids removal unit 238. The reduced-solids stream 246 may be solids-free.

The cleanup section 234 may include piping and valving to allow flexibility in routing streams to and through the various units of the cleanup section 234. Such piping and valving is not shown in FIG. 2 for simplicity. Flow through the various units in the cleanup section 234 may be organized in any way provided by the piping configurations of various embodiments. For example, the reduced-solids stream 246 may be routed to the sulfate treatment unit 240 or to the additional cleanup units 242, and effluent from the sulfate treatment unit 240 may be routed to the solids removal unit 238 or to the additional cleanup units 242, and effluent from any of the additional cleanup units 242 can be routed to the solids removal unit 238 or to the sulfate treatment unit 240. Thus, although piping and valving for delivering streams to and from the sulfate treatment unit 240 and the additional cleanup unit or units 242 are not shown in FIG. 2, such piping and valves should be understood as being ascertainable by those skilled in the relevant art.

The sulfate treatment unit 240 uses a sulfate precipitation reagent stream 248 that comprises calcium chloride, and may also include barium chloride in some embodiments, to reduce the presence of dissolved sulfate ions. In some cases the sulfate precipitation reagent stream 248 is a solution of calcium chloride. Calcium chloride solution is mixed with the stream provided to the sulfate treatment unit 240, and the mixture is allowed to react to yield calcium sulfate, at least some of which may precipitate as a solid salt. Sulfate treatment may be performed between divalent treatment and solids removal, so that precipitated calcium sulfate can be removed in the solids removal unit 238. Alternately, sulfate treatment may be performed after solids removal, and any solids resulting from sulfate treatment can be removed upon recycle of said solids into the treatment stream 226.

The additional cleanup unit or units 242 may include a carboxylate removal unit. The carboxylate removal unit uses an acidifying reagent, such as a strong acid solution, to lower pH of a stream containing carboxylates to a level that converts some or all of the carboxylates into conjugate carboxylic acids. The acidifying reagent is provided to the carboxylate removal unit in a cleanup reagent stream 250, which may include other cleanup reagents to the extent such agents are not incompatible with acidifying reagents. The carboxylate removal unit also has a vaporizing unit to vaporize the carboxylic acids. Following removal of the carboxylic acids, the carboxylate removal unit may have a neutralizing section to restore pH of the stream to a more neutral value.

Sulfate treatment is most efficient where sulfates tend to be highest in solution concentration. In most cases, the highest concentration of sulfates in a liquid stream of a MEG recovery process can be found in the liquid left behind where MEG and water are vaporized, after divalent cations are removed from the liquid. In many cases, removal of solids in the solids removal unit carries away enough sulfate concentration that the mass of sulfate in the feed to the MEG recovery process is less than that leaving in the solids removal unit. In such cases, sulfate treatment is not needed because sulfate does not accumulate. Where sulfate accumulates, however, sulfate treatment is most effective, as mentioned above, at locations where sulfate concentration is highest. Typically, where sulfate concentration in a liquid stream of a MEG recovery unit reaches at least about 550 ppm, a sulfate treatment using calcium chloride can reduce the solution sulfate concentration by precipitating calcium sulfate. The sulfate treatment process may also use temperature to reduce sulfate, for example by heating a sulfate-containing stream treated with calcium chloride to reduce the solubility of calcium sulfate and by subjecting the treated stream to solids removal at an elevated temperature. For example, calcium concentration can be reduced by increasing temperature from 25° C. to 80° C. Where sulfate treatment is followed by solids removal, temperature can be increased for the solids removal to precipitate incrementally more solids. If sulfate concentration is below about 550 ppm, barium chloride may be used, or the sulfate concentration may be tolerated until a level is reached where calcium chloride can be effective.

Figure 3:
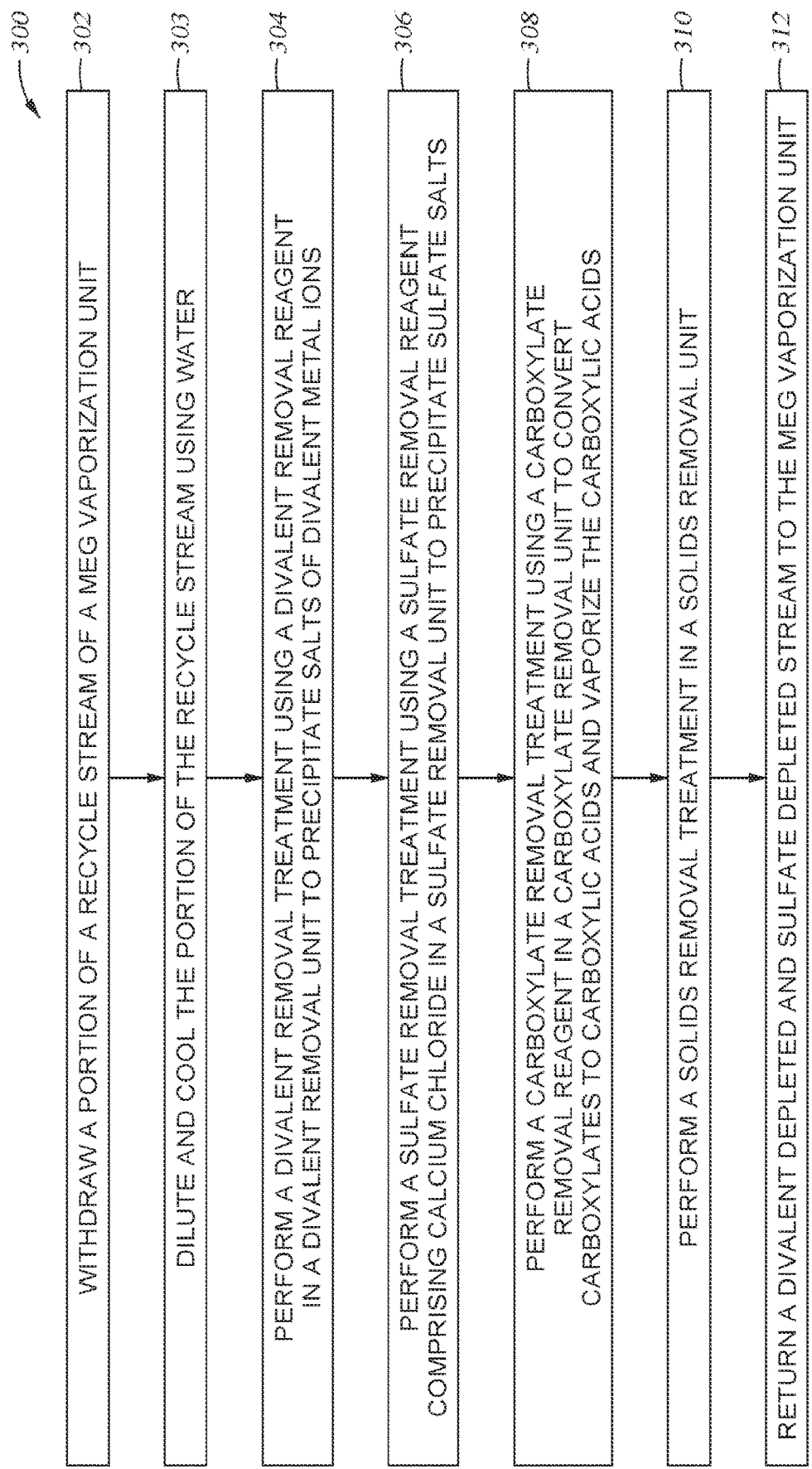
FIG. 3 is a flow diagram summarizing a method according to one embodiment.

FIG. 3 is a flow diagram summarizing a method 300 according to one embodiment. The method 300 is a method of treating a stream in a MEG recovery unit. At 302, a portion of a recycle stream of a MEG vaporization unit is withdrawn. The MEG vaporization unit is operated to vaporize MEG and water from a rich MEG stream comprising MEG, water, solids, dissolved and undissolved salts, optionally trace hydrocarbons, and impurities such as carboxylates. Here, the rich MEG stream contains an amount of a sulfate impurity that is above a threshold for steady-state sulfate concentration in the MEG recovery unit. Heat is typically provided by heating the recycle stream and returning the heated recycle stream to the vaporization unit.

At 303, water is added to the portion of the recycle stream to cool and dilute the stream. The divalent treatment described below at 304 can bring adverse conditions if performed on relatively hot and concentrated divalent cation streams at high MEG content, so the divalent cation concentration, the MEG concentration, and the temperature of the portion of the recycle stream is reduced by adding water prior to the divalent treatment. The amount of water added can be controlled by measuring a parameter of the stream representative of divalent cation concentration and adjusting the amount of water added based on the measured parameter. In some cases, the portion of the recycle stream is diluted 50% by volume, while in other cases the amount of water used is less. Water burden can be minimized by measuring a parameter of the divalent treated stream to determine a condition of the divalent treated stream and controlling the amount of water added based on the measured parameter. For example, in some cases viscosity of the feed to, or effluent from, the divalent treatment can be measured, and flow of dilution stream, water or other streams, can be controlled based on the measured viscosity. In some cases, increasing viscosity can indicate a need for more dilution. A control system can implement machine learning to minimize the amount of water added, based on parameters representing divalent concentration and/or parameters representing condition of the divalent treated stream.

At 304, the portion of the recycle stream is provided to a divalent treatment unit where the portion of the recycle stream is treated with a divalent precipitation reagent to precipitate salts of divalent metal ions. The divalent precipitation reagent is an alkalinity reagent, and may comprise alkaline components such as carbonates, bicarbonates, and/or hydroxides of alkali metal ions such as sodium and potassium. The divalent precipitation reagent is mixed with the portion of the recycle stream and allowed time to react at a nominal temperature. The reaction forms a divalent treated stream, which comprises a liquid depleted in divalent cations and a divalent-rich solid phase. The divalent precipitation reagent may be added in a stoichiometric amount, with an amount of alkaline component molecules substantially equal to twice the amount of divalent cations in the portion of the recycle stream for hydroxide reagents and the amount of alkaline component molecules substantially equal to the amount of divalent cations in the portion of the recycle stream for carbonate reagents. Alternately, the portion of the recycle stream may be underdosed or overdosed with divalent precipitation reagent. Underdosing is providing a reagent amount below the stoichiometric equivalent amount and overdosing is providing an excess amount of a reagent above the stoichiometric equivalent amount.

An amount of divalent precipitation reagent to be used may be determined by analyzing (e.g. titrating, either manually or automatically) a portion of the feed to the divalent treatment unit or a portion of the effluent of the divalent treatment unit. Analysis of the feed to the divalent treatment unit can be used to calculate a stoichiometric dose, an overdose, or an underdose of divalent precipitation agent. Analysis of the effluent from the divalent treatment unit can be used to adjust the dose, if desired, in a feedback control. Alternately, pH of the mixture can be used to control the amount of divalent precipitation reagent added to the process. In such cases, the pH is typically controlled at a level of 8 or more, for example 10 or more, by adjusting the rate of addition of alkaline reagents.

At 306, the divalent treated stream is provided to a sulfate treatment unit, where the divalent treated stream is treated with a sulfate precipitation reagent to precipitate sulfate salts and produce a sulfate treated stream. The sulfate precipitation reagent comprises calcium chloride. The sulfate precipitation reagent may be a calcium chloride solution in water. The sulfate precipitation reagent may be a calcium chloride solution in an aqueous medium that may or may not include water. The sulfate precipitation reagent may be a mixed solution of calcium chloride and barium chloride in water. The sulfate precipitation reagent may be a mixed solution of calcium chloride and barium chloride in an aqueous medium that may or may not include water. Concentration of calcium chloride in the sulfate precipitation reagent may be any value up to the solubility limit of calcium chloride in the medium. Likewise, concentration of barium chloride in the sulfate precipitation reagent may be any value up to the solubility limit of barium chloride in the calcium chloride solution. The sulfate precipitation reagent is mixed with the divalent treated stream and allowed to react at a nominal temperature. Calcium, and optionally barium, ions in the sulfate precipitation reagent react with sulfate ions in the divalent treated stream to form salts of calcium and barium sulfate. Barium sulfate, to the extent barium is used, is insoluble and precipitates. Calcium sulfate is more soluble in water than barium sulfate, so some calcium may remain in solution with sulfate, but most precipitates as calcium sulfate salt.

Where sulfate precipitation follows divalent precipitation, the divalent treatment process will have reduced the calcium ion content in the liquid portion of the stream subjected to sulfate treatment. In such cases, adding calcium chloride, optionally with barium chloride, precipitates sulfates and usually leaves some calcium ion content, and perhaps some barium ion content, in the remaining liquid. As described herein, performing the various cleanup operations described herein on a recycle stream allows for the overall calcium, and optionally barium, ion content to be controlled as the vaporization process is circulated.

Sulfate precipitation reagent may be added in stoichiometric quantity by adding the same number of calcium chloride and barium chloride molecules as sulfate ions in the divalent treated stream. Alternately, sulfate precipitation reagent may be provided in an overdose or an underdose. Typically, when sulfate treatment follows divalent treatment, sulfate precipitation reagent is provided in a stoichiometric dose or an underdose to avoid adding back divalent cations that were just removed in divalent precipitation. In one embodiment, sulfate precipitation reagent is provided at an equivalency of 90%, which means that 90% of the sulfate precipitation reagent enabling to completely remove sulfate from the liquid solution is added. Also, typically, residual calcium concentration in the sulfate treated stream is less than about 500 ppm, for example less than about 200 ppm, depending on the amount of calcium chloride used to treat sulfates. Residual calcium is maintained at a low level by balancing divalent precipitation with calcium chloride addition to treat sulfates. Overdose can also be used in some situations, and dosing can change from underdosing to overdosing, or vice versa, temporarily as process conditions change. For example, overdosing can be used where concentration of divalent cations is relatively low and concentration of sulfate ions is relatively high. Overdosing can generally be tolerated where divalent removal capacity is high enough to manage the extra cations added by overdosing.

An underdose of calcium chloride may be any level, from about 50% equivalency up to 99% equivalency. For example, in some cases the underdose may be from 60% equivalency to 80% equivalency. The underdose level determines the level of residual sulfate (FIG. 4) and calcium (FIG. 5) left in the process, a small amount of which may be tolerable in some processes. If the sulfate excess in the process is small, then the amount of calcium chloride added to reduce sulfate may be much less that a stoichiometric amount based on the amount of sulfate ions present. A small calcium chloride treatment may suffice to prevent a rise of sulfate ions. In some cases, an amount of sulfate excess may be determined by comparing successive sulfate analyses of a stream to determine a rate of increase in sulfate concentration, if any. The rate of sulfate concentration increase may be resolved as a mass per unit time. A rate of calcium chloride addition may then be computed as the molar equivalent of the resolved sulfate concentration increase rate. The computed amount of calcium chloride, in comparison to the total amount of sulfate ions present, may turn out to be any level of equivalency, from a very low level (e.g. less than 10%) to a level approaching 100%.

Sulfates and divalent cations are precipitated by the sulfate and divalent treatments, but are not removed until solids removal is performed. Precipitated sulfate salts and salts of divalent metal ions are carried as solids in the stream until the solids are removed. After solids removal, the resulting stream is depleted of divalent cations and sulfate ions. Carboxylates, in contrast, are removed in the carboxylate removal operation, because the carboxylate removal operation converts carboxylates to volatile carboxylic acids that can be removed by evaporation.

At 310, a solids removal treatment is performed to remove solids produced by divalent treatment and/or sulfate treatment. Any of the divalent treated stream, the sulfate treated stream, or the carboxylate depleted stream can be routed to a solids removal unit to remove solids, with the proviso that divalent solids produced by divalent treatment will be redissolved by carboxylate treatment if not removed before exposure to acid. It should be noted that carboxylate removal can be performed before and/or after solids removal. Where divalent cations are precipitated, the resulting divalent solids are removed by solids removal treatment before any subsequent acid processing. Any technique, or combination of techniques, for removing solids, such as filtration and density separation, can be used to remove solids. Such techniques include microfiltration, ultrafiltration, nanofiltration, membrane separation, and rotational separation, such as cyclone or centrifuge separation, can be used. Solids are routed to any convenient disposal, and the solids removal unit yields a solids depleted stream, which is also depleted of divalent cations and sulfate ions, if divalent and sulfate treatment preceded solids removal.

At 308, an optional carboxylate removal treatment can be performed. The sulfate treated stream can be provided to a carboxylate removal unit, before or after solids are removed. Alternately, divalent treated stream can be provided to the carboxylate removal unit at 308 after divalent solids are removed. The stream provided to the carboxylate removal unit is treated with a carboxylate removal reagent to remove carboxylates. The carboxylate removal operation of 308 is shown in dashed line as an optional treatment. The carboxylate removal reagent includes a strong acid that can convert carboxylate to conjugate carboxylic acids, which can be vaporized. The strong acid lowers pH of the treated stream to 4 or less to convert the carboxylates to carboxylic acids. The carboxylic acids are more volatile than the carboxylates, and can in many cases be readily vaporized to yield a carboxylate depleted stream, which may be a carboxylate and sulfate depleted stream if sulfates have been removed prior to carboxylate treatment.

At 312, any of the various treated and/or depleted streams are returned to the MEG vaporization unit in the recycle portion of the unit. The return streams can be mixed with new feed to the MEG vaporization unit, if desired. The return streams may be returned to the MEG vaporization recycle prior to heating or after heating. Typically, heating of the recycle is controlled by a temperature, which may be measured in the liquid pool of the MEG vaporization unit or in the return stream to the MEG vaporization unit.

Sulfate, and optionally carboxylate, treatment can be performed intermittently. Divalent removal is more often continuous, although divalent removal can also be performed intermittently. The relative frequency of divalent cation removal, sulfate removal, and carboxylate removal depends on the relative proportion of divalent cations, sulfate anions, and carboxylates in the MEG stream. Divalent cations tend to be more plentiful, so divalent removal is typically performed more frequently than sulfate or carboxylate removal, although all removal processes can be performed continuously. Thus, any or all of divalent removal, sulfate removal, and carboxylate removal can be performed in a continuous, batch, or semi-batch manner. Ion content of one or more streams can be analyzed to determine the need for an ion treatment, such as divalent removal, sulfate removal, and or carboxylate removal. The analysis may be performed automatically using an auto-titrator analyzer, or by manually titrating samples. A controller can be employed to collect signals from an auto-titrator or receive input from a laboratory analysis system or receive manual input of analysis results and determine whether any portion of the recycle should be subjected to an ion treatment. In some cases, the results may indicate the recycle needs any or all of divalent removal, sulfate removal, and/or carboxylate removal. A portion of the recycle stream can be directed to any removal units needed for ion treatment.

Divalent removal, sulfate removal, carboxylate removal, and solids removal can all be performed concurrently in separate units, either in serial or parallel configuration, or any combination thereof, using any appropriate treatments (e.g. pH adjustment), with the proviso that divalent metal salt solids from a divalent treatment should be removed prior to lowering pH for carboxylate removal. Sulfate treatment using calcium chloride can be performed in the same unit as carboxylate removal, if desired. The sulfate precipitation reagent and the carboxylate removal reagent are both added to the same mixture, and carboxylates revert to acids and evaporate while sulfates precipitate. The resulting mixture can be treated with pH adjustment reagents to control the relative amount of carboxylate conversion to volatile acids and calcium sulfate precipitation. For example, pH of the mixture can be controlled to a range around 4.0 to 4.5, and can be lowered to favor carboxylate conversion at the expense of calcium sulfate dissolution, or raised to favor calcium sulfate precipitation at the expense of carboxylate conversion. In this way, as process conditions change, carboxylate removal and sulfate removal can be balanced.

A control system for MEG recovery may monitor sulfate ion content and calcium ion content of any stream, and may adjust divalent removal and sulfate removal based on the results. Analysis results indicating high and/or growing sulfate ion content can trigger sulfate removal, or increased flow of sulfate precipitation reagent to the sulfate treatment unit. Analysis results indicating tolerable, or low, sulfate ion content can trigger decreased flow of sulfate precipitation reagent or discontinuation of sulfate removal. Analysis results indicating high and/or growing calcium ion content can trigger divalent removal, or increased flow of divalent precipitation reagent to the divalent treatment unit. Analysis results indicating tolerable, or low, calcium ion content can trigger decreased flow of divalent precipitation reagent or discontinuation of divalent removal.

In some cases, barium chloride can be used along with calcium chloride for sulfate treatment, together in one operation or in separate operations. For example, calcium chloride can be used for the majority of sulfate treatment, and smaller amounts of barium chloride can be used to treat very low residual levels of sulfate ions remaining in solution after calcium chloride addition and/or to reduce solution sulfate concentration to very low levels. In the example described above where sulfate and calcium ion concentrations are monitored, calcium can be added to treat high sulfate ion levels until a maximum calcium ion concentration is reached (or until a minimum sulfate ion concentration is reached), and if further sulfate treatment is needed, a small amount of barium chloride can be added to complete the sulfate treatment. The barium chloride addition can be performed in the same treatment unit as the calcium chloride addition, or in a second treatment unit.

Calcium chloride has advantages, as a sulfate precipitation reagent, over barium chloride. The higher solubility of calcium chloride in water allows for use of a sulfate precipitation reagent that has less water. Adding less water to the process means less water has to be circulated, heated, cooled, and removed, leading to smaller equipment and lower energy budget. The lower molecular weight of calcium chloride also allows less overall mass to be used to treat sulfate ions. It should be noted that other calcium halides, such as calcium bromide and/or calcium iodide, can also be used instead of, or in addition to, calcium chloride, and also with barium chloride. If carboxylate removal is to be used, calcium carboxylates can also be used where the conjugate carboxylic acid of the carboxylate has a boiling point lower than the corresponding boiling point (i.e. at the same pressure) of MEG so that the carboxylate can be converted to acid and removed using the carboxylate removal described herein. Examples of such calcium carboxylates include, but are not limited to, calcium formate, calcium acetate, and calcium citrate. For purposes herein, these calcium carboxylates will be called "lower calcium carboxylates," reflecting the "lower" boiling point of the conjugate acids. Mixtures of calcium halides and lower calcium carboxylates can also be used, also along with barium chloride. Where calcium compounds other than calcium chloride are used, "underdosing" has the same meaning as set forth above.

Figure 4:
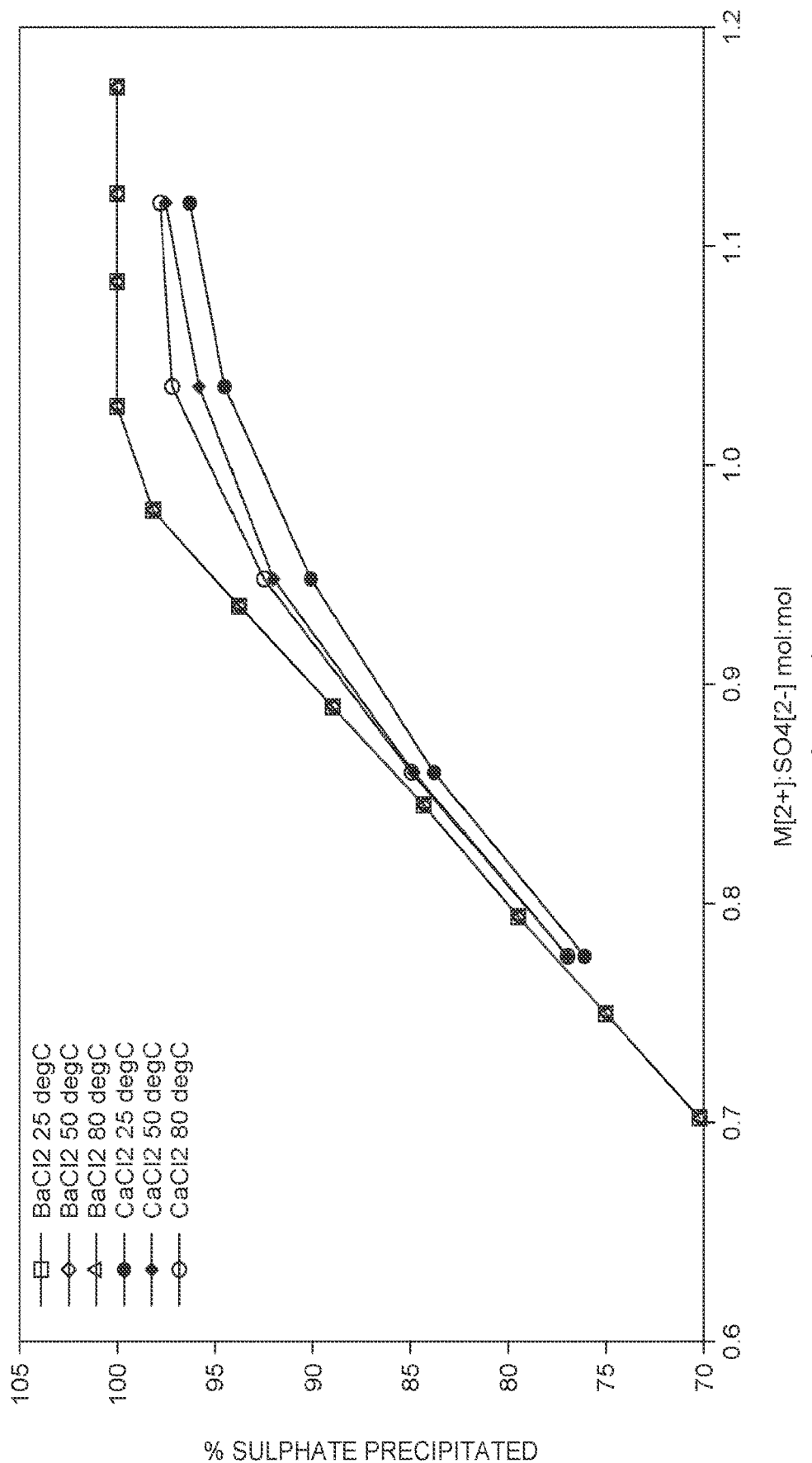
FIG. 4 is a graph showing sulfate removal efficiency versus molar ratio of barium or calcium cation to sulfate anion.

Calcium chloride and barium chloride treatments were simulated using a rich MEG stream composition of 500 kg water, 500 kg MEG, 15 kg NaCl, and 35 kg $Na_2SO_4$. FIG. 4 is a graph showing sulfate precipitation efficiency versus molar ratio of barium or calcium cation to sulfate anion. FIG. 4 shows that barium chloride is somewhat more effective at precipitating sulfate than calcium chloride, but as described above, calcium chloride has other advantages over barium chloride. FIG. 4 shows that the effectiveness of calcium chloride is good, although not quite as good as barium chloride.

Figure 5:
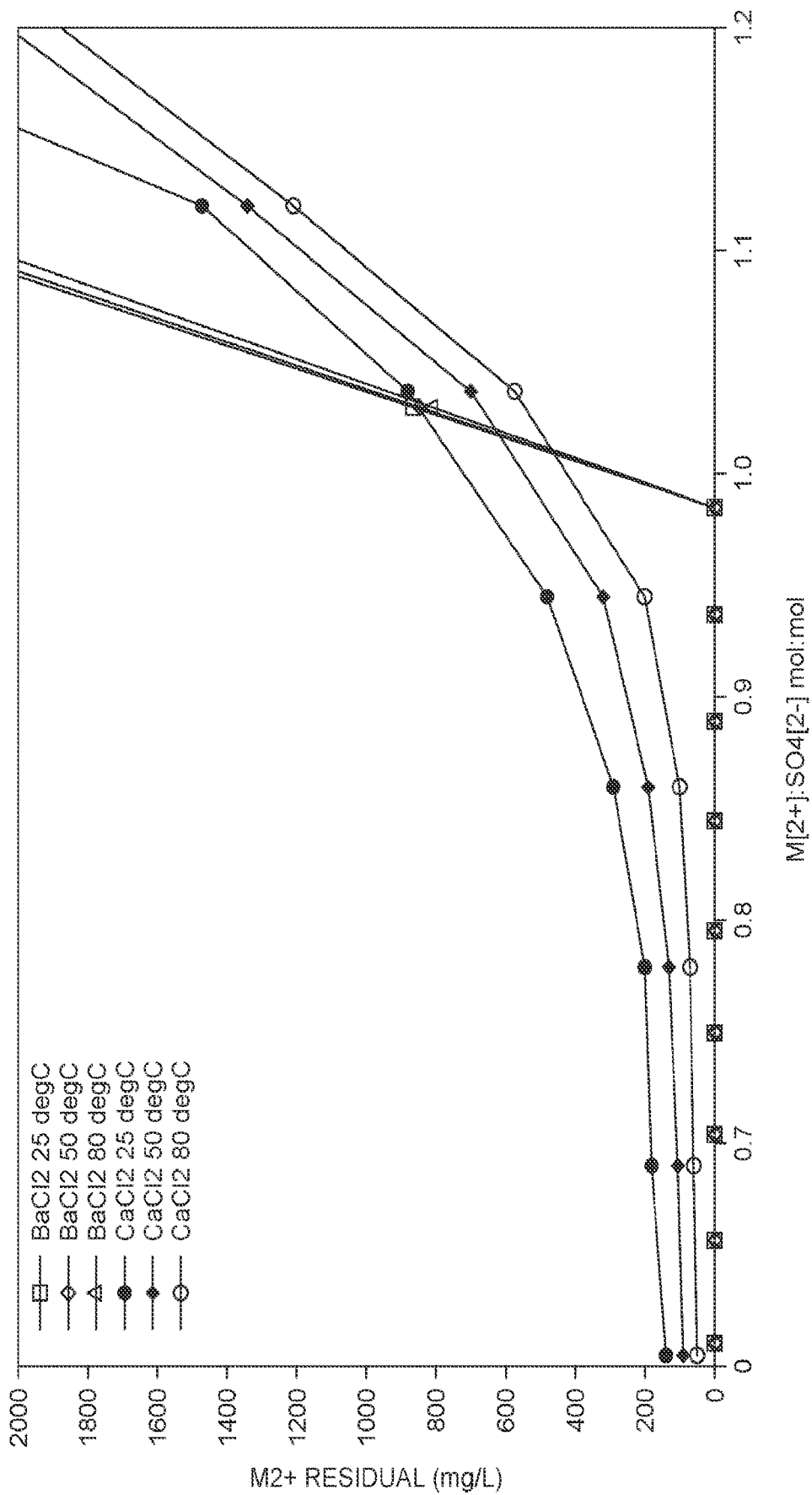
FIG. 5 is a graph showing residual cation content after sulfate treatment using barium chloride and/or calcium chloride, versus molar ratio of cation to sulfate anion.

FIG. 5 is a graph showing residual cation content after sulfate treatment using barium chloride and/or calcium chloride, versus molar ratio of cation to sulfate anion. Residual calcium content rises more quickly, as the molar ratio increases, than does barium content, but many MEG recovery processes may be tolerant to a low level of calcium circulating through the process. For example, in some cases a residual calcium content of 200 ppm may be tolerable. As described above, a portion of the MEG vaporization recycle can be continuously circulated to divalent removal to keep calcium concentration at or near a target level as sulfate treatment adds calcium to the process.

Figure 6:
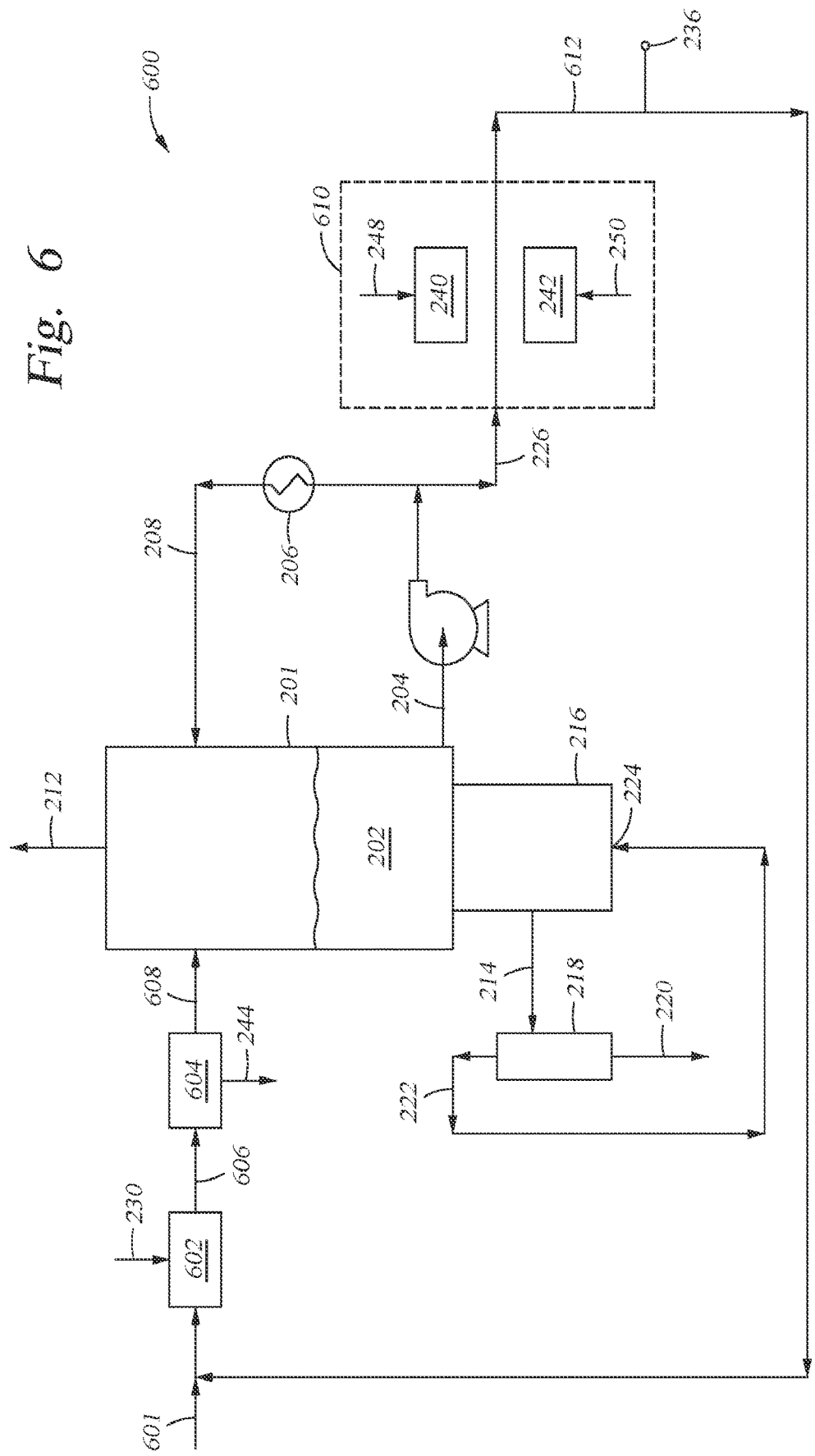
FIG. 6 is a schematic process diagram summarizing a MEG vaporization process with sulfate removal according to another embodiment.

FIG. 6 is a schematic process diagram summarizing a MEG vaporization process 600 with sulfate removal according to another embodiment. The process 600 may be used as the vaporization 104 of the process 100 of FIG. 1. Like the process 200, the process 600 includes the vaporization vessel 201 to vaporize a MEG/water mixture, which is withdrawn through the overhead line 212, from the liquid pool 202. In this case, however, divalent removal is performed prior to the vaporization. Here, a divalent treatment unit 602 receives a rich MEG/water stream 601 along with the divalent precipitation reagent 230 and sends a divalent treated stream 606 to a solids removal unit 604, where the solids removal stream 244 is removed. The solids removal unit 604 yields a divalent depleted stream 608 which is routed to the vessel 201.

In this case, the treatment stream 226 is withdrawn from the recycle 204 and routed to a cleanup section 610 that has the sulfate treatment unit 240 and, optionally, the carboxylate removal unit 242. Alternately, the cleanup section 610 may be a single unit for both sulfate treatment and carboxylate removal in a single vessel. In this case, the effluent 612 of the cleanup section 610 is routed back to the divalent treatment unit 602 to remove residual calcium left after sulfate treatment using calcium chloride, and all solids produced by divalent precipitation and sulfate precipitation are removed in the solids removal unit 604 upstream of the vaporization vessel 201.

The process 600 has the advantage, relative to the process 200, that divalent cations, and any potential scaling that might occur from precipitation of divalent cations, is removed prior to vaporization processing. The stream treated in divalent removal is larger in volume, potentially resulting in larger equipment and larger flow of divalent precipitation reagent, but in some cases the benefit of reduced exposure of equipment to potential scaling more than offsets the cost of any larger divalent removal burden. The process 600 also has the advantage that a potential for excess calcium introduced in sulfate treatment is mitigated by recycling sulfate treated fluid to upstream divalent treatment and solids removal, thus removing incentive to underdose the sulfate treatment operation.

Figure 7:
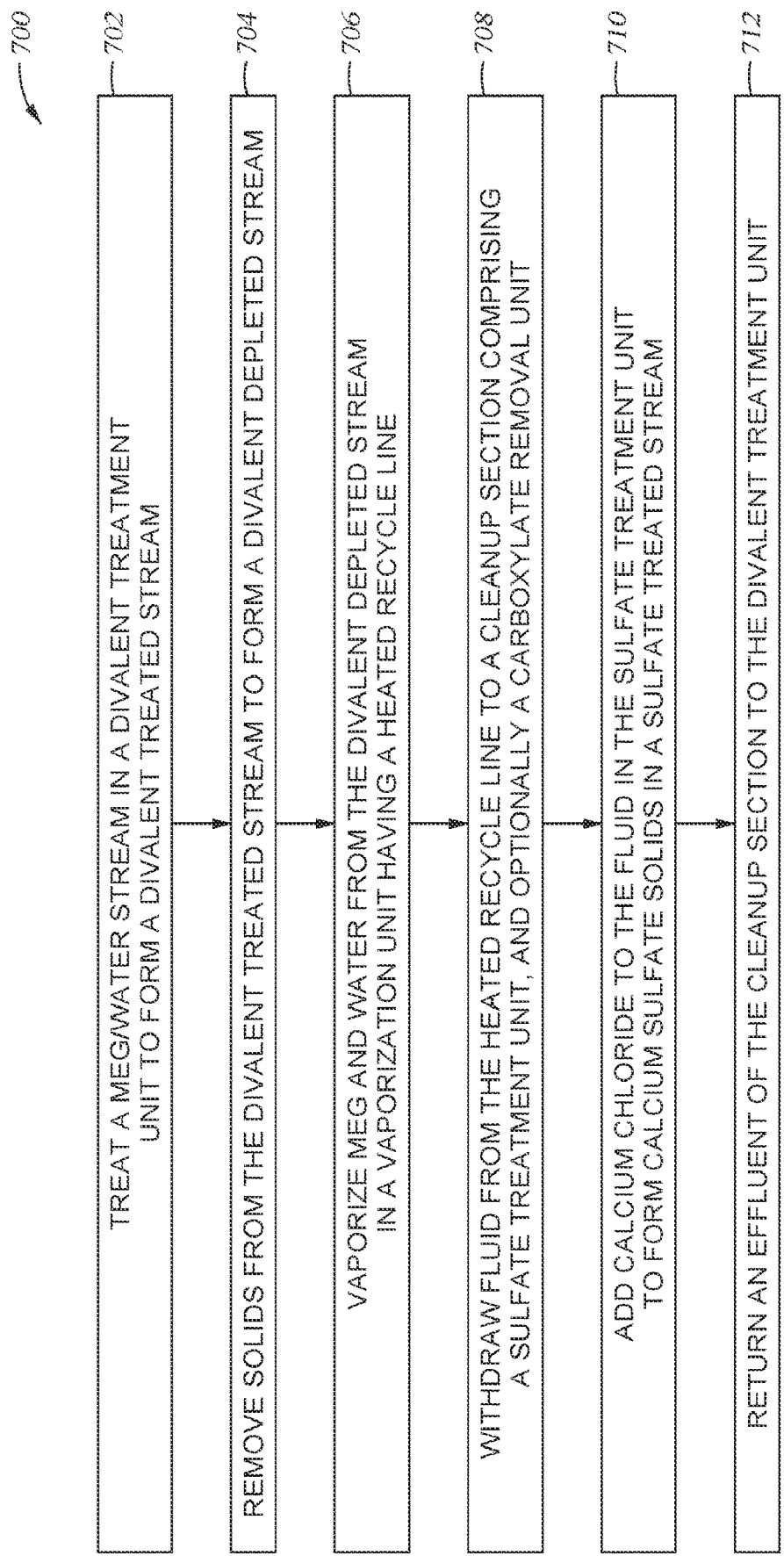
FIG. 7 is a flow diagram summarizing a method according to another embodiment.

FIG. 7 is a flow diagram summarizing a method 700 according to another embodiment. The method 700 is a method of treating a stream in a MEG recovery unit. At 702, a MEG/water stream is treated in a divalent treatment unit to form a divalent treated stream. As described above, a divalent precipitation reagent is added to the MEG/water stream in quantity sufficient to precipitate substantially all divalent cations from the MEG/water stream as hydroxide and/or carbonate solids. The divalent precipitation reagent, as above comprising alkalinity reagents such as sodium or potassium hydroxide, carbonate, and/or bicarbonate. A divalent treated stream is formed in the divalent treatment unit and is routed to a solids removal unit.

At 704 solids are removed in the solids removal unit to form a divalent depleted stream and a solids removal stream. Solids removal technology is used that can accommodate a larger flow of fluid.

At 706 the divalent depleted stream is routed to a vaporization unit having a heated recycle line, where MEG and water are vaporized. A recycle is withdrawn from a liquid pool maintained in the vaporization unit, is passed through a heater, and is returned to the vaporization unit to maintain temperature in the vaporization unit. MEG and water are vaporized and removed from the vaporizer, and the remaining liquid is concentrated in monovalent salts, which typically precipitate as solids and are removed in a solids removal unit to maintain composition of the liquid pool.

At 708, fluid is withdrawn from the heated recycle line in a treatment stream, which is routed to a cleanup section comprising a sulfate treatment unit, and optionally a carboxylate removal unit. Alternately the cleanup section may comprise a single impurity treatment that addresses both sulfate impurities and carboxylate impurities in a single vessel, converting and vaporizing carboxylic acids and precipitating sulfate salts at the same time in one vessel.

At 710, calcium chloride is added to the fluid in the sulfate treatment unit to form calcium sulfate solids in a sulfate treated stream. Where the cleanup section comprises a single vessel, the single vessel may be used for sulfate treatment, or the single vessel may be used for sulfate treatment and for carboxylate treatment. Where the single vessel is used for sulfate treatment, a sulfate precipitation reagent comprising calcium chloride is added to the treatment stream and mixed with the treatment stream to precipitate calcium sulfate salts. Where the single vessel is used for sulfate treatment and carboxylate treatment, a treatment reagent comprising calcium chloride and a strong acid, for example hydrochloric acid, is added to the treatment stream and mixed with the treatment stream. The mixture is given time to react, in which calcium sulfate salts precipitate and carboxylic acids converted from carboxylates vaporize. The mixture is maintained at a temperature that evaporates carboxylic acids, which are removed as a vapor stream. The single vessel yields a fluid depleted of dissolved sulfates and containing precipitated calcium sulfate salts. The fluid may also be depleted of carboxylates. If desired, the low pH fluid emerging from carboxylate treatment may be neutralized.

Where the cleanup section comprises more than one treatment vessel, a first vessel may be used for a first treatment and a second vessel used for a second treatment. The first and second treatments are sulfate treatment and carboxylate treatment, and may be performed in any series order, or concurrently in parallel. In other embodiments, both the first and second treatment may be sulfate treatments, where the first treatment is a coarse sulfate treatment and the second treatment is a fine sulfate treatment. Such embodiments may occur where sulfate levels are high. In such cases, calcium chloride can be used as a first sulfate treatment to reduce sulfate levels and barium chloride, or a mixture of calcium and barium chloride, can be used as the second sulfate treatment to further reduce, or eliminate, sulfates.

At 712, an effluent of the cleanup section is returned to the divalent treatment unit. Any excess calcium remaining in the effluent is treated in the divalent treatment unit. Thus, an amount of calcium chloride used for sulfate treatment need not be an underdose, because any residual calcium (or barium if barium is also used) is removed in the divalent treatment unit.

FIG. 8 is a schematic process diagram summarizing a MEG recovery process 800 according to another embodiment. The process 800 has a hydrocarbon separation 802 that receives a crude MEG stream 801 and yields a hydrocarbon vapor stream 804, a hydrocarbon liquid stream 806, and a rich MEG stream 808. The process 800 has a divalent removal unit 810 that receives the rich MEG stream 808 and yields a divalent depleted MEG stream 812 and a removed divalent stream 814. The divalent removal unit 810 includes a divalent treatment unit 816, where a divalent precipitation reagent is added to the rich MEG stream 808 to precipitate divalent cations as salts, and a solids removal unit 818, where the solids are removed to yield the divalent depleted MEG stream 812 and the removed divalent stream 814. This divalent removal unit 810 is optional, and can be omitted.

The process 800 has a water separation 820, which may be a distillation or other thermodynamic separation unit. The water separation 820 yields a water stream 822 and a lean MEG stream 824. The lean MEG stream 824 typically includes MEG and dissolved salts.

The process 800 has a MEG purification 826 that receives all, or a portion of, the lean MEG stream 824 and yields a purified MEG stream 828. Where a portion of the lean MEG stream 824 is purified, a first portion 830 of the lean MEG stream 824 is provided to the purification 826, and a second portion 832 of the lean MEG stream 824 is not provided to the purification 826, but bypasses the purification 826. The purified MEG stream 828 can be mixed with the second portion 832 to yield a MEG product stream 834. Where all the lean MEG stream 824 is purified, the purified MEG stream 828 and the MEG product stream 834 are the same. Where only the first portion 830 is purified, the MEG product stream 834 is a mixture of the second portion 832 and the purified MEG stream 828. Thus, the MEG purification 826 can be used to reduce impurities, such as monovalent cations, divalent cations, sulfate ions, and carboxylate ions in all, or part, of the lean MEG stream 824. Typically, the first portion 830 has a flow rate that is 30 to 50% of a flow rate of the lean MEG stream 824, or lower, and the second portion 832 has a flow rate that is 50 to 70% of the flow rate of the lean MEG stream 824, or higher. In one case, the flow rate of the first portion 830 is 5% of the flow rate of the lean MEG stream 824, and the flow rate of the second portion 832 is 95% of the flow rate of the lean MEG stream.

The MEG purification 826 includes a vaporization 840 that precipitates solids and produces the purified MEG stream 828. The vaporization 840 includes a heated recycle 842 to provide energy for the vaporization. A treatment stream 844 is withdrawn from the heated recycle 842 and routed to a cleanup section 846, which includes sulfate treatment and solids removal, for removal of at least sulfate solids and monovalent salt solids, and can optionally include divalent treatment and/or carboxylate removal if desired. The solids removal can also include capability to remove divalent solids. The cleanup section 846 yields a treated stream 848 that is returned to the vaporization 840 or the pheated recycle 842. The purified MEG stream 828 results from vaporization of MEG in the vaporization 840.

The cleanup section 846 is illustrated here as a singular plant, unit, or installation, but it is envisioned that operations of the cleanup section 846 might not be co-located. For example, solids removal for sulfates and monovalent salts may be provided in separate solids removal apparatus or stages (alternately, one solids removal unit can be used in batch mode, alternating services). The solids removal for monovalent salts may be at a different location from the solids removal for sulfates, and indeed from the rest of the equipment of the cleanup section 846. Here, the cleanup section 846 is envisioned as a collection of equipment to manage the composition of the fluids inside the vaporization 840, and may be co-located, in total or in part, or spatially distributed at different locations. Although in some instances, co-location of the equipment of the cleanup section 846 may offer some advantages, the illustration here is not intended to express that the equipment of the cleanup section 846 must be co-located.

A portion of any stream in the MEG purification 826 can be recycled to the divalent removal unit 810 to maintain a low level of divalent cations in the purified MEG stream 828. Where divalent cations are added in the cleanup section 846 to treat sulfate ions, those divalent cations can optionally be removed by providing a recycle 864 to the divalent treatment of the cleanup section 846, or by recycling a stream to the divalent removal unit 810. Here, the recycle 864 is shown recycling to the divalent removal unit 810. The recycle 864 can also serve as the dilution and cooling referred to in connection with the method 300. Use of make-up water can be reduced in this way. Additionally, the water stream 822 separated in the water separation 820 could optionally be used to dilute the rich MEG stream 808 for treatment in the divalent removal unit 810, if desired for a particular implementation, or to dilute any other stream that might benefit from dilution. Where the rich MEG stream 808 is diluted before divalent treatment, the resulting stream provided to the divalent removal unit 810 may be termed a dilute MEG stream.

The cleanup section 846 may have a first solids removal for removing monovalent solids of the vaporization 840 and a second solids removal for removing solids from divalent and sulfate treatment. A solids-containing stream 841 may be removed from a lower portion of the vaporization 840 and routed to the cleanup section 846 for solids removal. Monovalent solid salts are removed, and a monovalent depleted stream returned to the lower portion of the vaporization 840.

The various operations of the cleanup section 846 can be performed in any order, except that removal of divalent salt solids, if any, should be done prior to any acid treatment, since acid treatment of divalent salt solids will re-dissolve the divalent salts. So, for example, sulfate treatment can be performed before or after carboxylate treatment. Sulfate solids removal can be performed before or after treatments for carboxylates and/or divalents. Monovalent removal can be performed concurrently with other processing in the cleanup section 846.

The process 800 can have a control system 850 to control relative volumes of the first portion 830 and the second portion 832 and volumes of any recycle streams within the cleanup section 846 and from the cleanup section to the divalent removal unit 810. A first composition sensor 852 can be provided in the MEG product stream 834 to reveal composition of the MEG product stream 834. A second composition sensor 856 can be provided in the rich MEG stream 808 to reveal composition of the rich MEG stream 808. The second composition sensor 856 can be located upstream or downstream of the mixing location of the recycle 864 with the rich MEG stream 808. A third composition sensor 858 can be provided in the divalent depleted MEG stream 812 to reveal composition of the divalent depleted MEG stream 812. A fourth composition sensor 860 can be provided in the lean MEG stream 824 to reveal composition of the lean MEG stream 824. At least one of the first, second, third, and fourth composition sensors is used for the control system 850, and any number, up to and including all, of the sensors can be used for the control system. Sensors can also be included in the cleanup section 846 to monitor performance thereof. A single sensor 866 is schematically shown at the cleanup section 846 to represent one or more sensors that can be used at convenient locations, for example at inlet or outlet streams of the various operations of the cleanup section.

The control system 850 has a controller 862 that is operatively coupled to the composition sensors 852, 856, 858, 860, and 866 to receive composition data, and to control elements of the process 800 for controlling compositions at various locations of the process 800. Flows to the MEG purification 826 can be controlled, flows of treatment reagents, such as divalent precipitation reagents, sulfate precipitation reagents, and carboxylate removal reagents, can be controlled, and recycle flows within the cleanup section 846 and from the cleanup section 846 to upstream locations, such as the divalent removal unit 810, can be controlled.

While the foregoing is directed to embodiments of the present disclosure, other and further embodiments of the present disclosure may be devised without departing from the basic scope thereof, and the scope thereof is determined by the claims that follow.

I claim:

1. A method of MEG recovery, comprising:
  withdrawing a portion of a recycle of a MEG vaporization unit;
  performing a divalent treatment on the portion of the recycle to reduce dissolved divalent cations in the portion of the recycle;
  performing a sulfate treatment to reduce dissolved sulfate ions in the portion of the recycle, the sulfate treatment comprising:
    adding an underdose of one or more calcium halides, one or more lower calcium carboxylates, or a mixture thereof, to a treatment stream; and
    precipitating calcium sulfate from the treatment stream;
  performing a solids removal treatment to reduce solids in the portion of the recycle; and
  returning the portion of the recycle, depleted in divalent cations, sulfate ions, and solids, to the MEG vaporization unit.

2. The method of claim 1, further comprising performing a carboxylate removal treatment to reduce carboxylates in the portion of the recycle.

3. The method of claim 2, wherein the carboxylate removal treatment and the precipitating calcium sulfate from the treatment stream are performed in the same vessel.

4. The method of claim 1, further comprising:
  mixing a portion of the recycle, depleted in divalent cations, with a rich MEG stream to form a dilute MEG stream;
  performing a divalent removal treatment on the dilute MEG stream to form a divalent depleted MEG stream;
  removing water from the divalent depleted MEG stream to form a lean MEG stream; and
  routing at least a portion of the lean MEG stream to the MEG vaporization unit.

5. The method of claim 1, further comprising performing a divalent removal on a rich MEG stream to form a divalent depleted MEG stream and routing at least a portion of the divalent depleted MEG stream to the MEG vaporization unit.

6. A method of MEG recovery, comprising:
  withdrawing a portion of a recycle of a MEG vaporization unit;
  performing a divalent treatment to reduce dissolved divalent cations in the portion of the recycle;
  performing a sulfate treatment to reduce dissolved sulfate ions in the portion of the recycle, the sulfate treatment comprising:
    adding an underdose of one or more calcium halides to a treatment stream; and
    precipitating calcium sulfate from the treatment stream;
  performing a solids removal treatment to reduce solids in the portion of the recycle;
  measuring a first parameter that represents concentration of calcium ions in the MEG vaporization unit;
  measuring a second parameter that represents concentration of sulfate ions in the MEG vaporization unit;
  controlling the sulfate treatment based on the second parameter;
  controlling the divalent treatment based on the first parameter; and
  returning the portion of the recycle, depleted in divalent cations, sulfate ions, and solids, to the MEG vaporization unit.

7. The method of claim 6, further comprising performing a carboxylate removal treatment to reduce carboxylates in the treatment stream.

8. The method of claim 6, wherein the divalent treatment, the sulfate treatment and the solids removal treatment are performed sequentially.

9. The method of claim 7, wherein the carboxylate removal treatment and the precipitating calcium sulfate from the treatment stream are performed in the same vessel.

10. The method of claim 6, further comprising:
  removing divalent cations, water, and solids from a lean MEG stream to form a rich MEG stream;
  mixing a portion of the recycle, after removing divalent cations, sulfate ions, and solids from the recycle, with the lean MEG stream; and
  routing the rich MEG stream to the MEG vaporization unit.

11. The method of claim 6, wherein the divalent treatment is performed before the sulfate treatment.

12. The method of claim 6, further comprising increasing a temperature of the treatment stream for the solids removal treatment.

13. The method of claim 9, further comprising adjusting pH of the treatment stream to control carboxylate removal and sulfate removal.

14. The method of claim 10, further comprising mixing a portion of the removed water with the lean MEG stream.

15. A method of MEG recovery, comprising:
treating a MEG stream in a divalent treatment unit to yield precipitated solids in a divalent treated stream;
performing a solids removal process on the divalent treated stream to form a divalent depleted stream;
vaporizing MEG from the divalent depleted stream in a vaporization unit having a heated recycle line;
withdrawing a fluid from the heated recycle line as a treatment stream;
performing a sulfate treatment to reduce sulfate ions in the treatment stream, the sulfate treatment comprising:
adding calcium chloride to the treatment stream; and
precipitating calcium sulfate from the treatment stream to form a sulfate treated stream; and
returning the sulfate treated stream to the divalent treatment unit.

16. The method of claim 15, further comprising performing a carboxylate removal treatment to reduce carboxylates in the treatment stream.

17. The method of claim 16, wherein the sulfate treatment and the carboxylate removal treatment are performed in the same vessel.

18. The method of claim 15, further comprising:
mixing a portion of the sulfate treated stream with the MEG stream prior to treatment in the divalent treatment unit.

19. The method of claim 15, further comprising separating water from the divalent depleted stream prior to vaporizing MEG from the divalent depleted stream.

20. The method of claim 19, further comprising mixing the separated water with the MEG stream prior to treating the MEG stream in the divalent treatment unit.

* * * * *